United States Patent
Troelsen et al.

(10) Patent No.: US 10,334,373 B2
(45) Date of Patent: Jun. 25, 2019

(54) HEARING DEVICE INCLUDING AN EXTERNAL ANTENNA PART AND AN INTERNAL ANTENNA PART

(71) Applicant: Oticon A/S, Smørum (DK)

(72) Inventors: Jens Troelsen, Smørum (DK); Rune Sø, Smørum (DK); Morten Thougaard, Smørum (DK)

(73) Assignee: Oticon A/S, Smørum (DK)

( * ) Notice: Subject to any disclaimer, the term of this patent is extended or adjusted under 35 U.S.C. 154(b) by 0 days.

(21) Appl. No.: 15/857,136

(22) Filed: Dec. 28, 2017

(65) Prior Publication Data

US 2018/0192212 A1    Jul. 5, 2018

(30) Foreign Application Priority Data

Dec. 29, 2016  (EP) .................................... 16207304
Feb. 8, 2017   (EP) .................................... 17155099

(51) Int. Cl.
*H04R 25/00* (2006.01)
*H04R 1/10* (2006.01)
(Continued)

(52) U.S. Cl.
CPC ....... *H04R 25/554* (2013.01); *A61N 1/36038* (2017.08); *A61N 5/0603* (2013.01); *H04R 1/1008* (2013.01); *H04R 25/505* (2013.01); *H04R 25/60* (2013.01); *A61N 2005/0605* (2013.01); *A61N 2005/0651* (2013.01); *H01Q 1/273* (2013.01); *H04R 2225/021* (2013.01); *H04R 2225/51* (2013.01); *H04R 2225/67* (2013.01)

(58) Field of Classification Search
None
See application file for complete search history.

(56) References Cited

U.S. PATENT DOCUMENTS 7,859,469 B1    12/2010  Rosener et al.
2009/0169038 A1  7/2009  Knudsen et al.
(Continued)

*Primary Examiner* — Paul W Huber
(74) *Attorney, Agent, or Firm* — Birch, Stewart, Kolasch & Birch, LLP

(57) ABSTRACT

The disclosure presents a method and a hearing device comprising a first portion adapted for being arranged behind an ear of a user for providing a signal, an output transducer for converting the signal to an acoustic output, a coupling element coupled to the first portion, and wherein the coupling element is adapted for transmitting at least the signal or the acoustic output. Furthermore, the hearing device comprises an antenna which includes an external antenna part and an internal antenna part, where the internal antenna part includes a first antenna element, a second antenna element where a first end of the second antenna element is arranged at one end of the first antenna element and is connected thereto, and where a second end of the second antenna element is connected to a ground plane, and a third antenna element which is spaced at a distance from the second antenna element and connected to the first antenna element, a feeding unit configured to supply a current to the antenna via the third antenna element, a wireless interface for receiving and/or sending data by means of the antenna, and wherein the coupling element comprises the external antenna part, and where the external antenna part is connected to the internal antenna part.

23 Claims, 10 Drawing Sheets

(51) Int. Cl.
  *A61N 1/36* (2006.01)
  *A61N 5/06* (2006.01)
  *H01Q 1/27* (2006.01)

(56) References Cited

U.S. PATENT DOCUMENTS

| | | |
|---|---|---|
| 2010/0321269 A1 | 12/2010 | Ishibana et al. |
| 2011/0032165 A1 | 2/2011 | Heng et al. |
| 2014/0185848 A1 | 7/2014 | Özden et al. |
| 2014/0328507 A1 | 11/2014 | Rabel et al. |

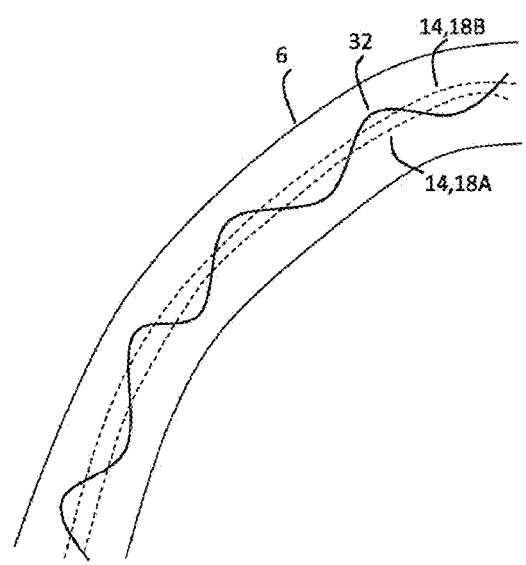
Figure 9
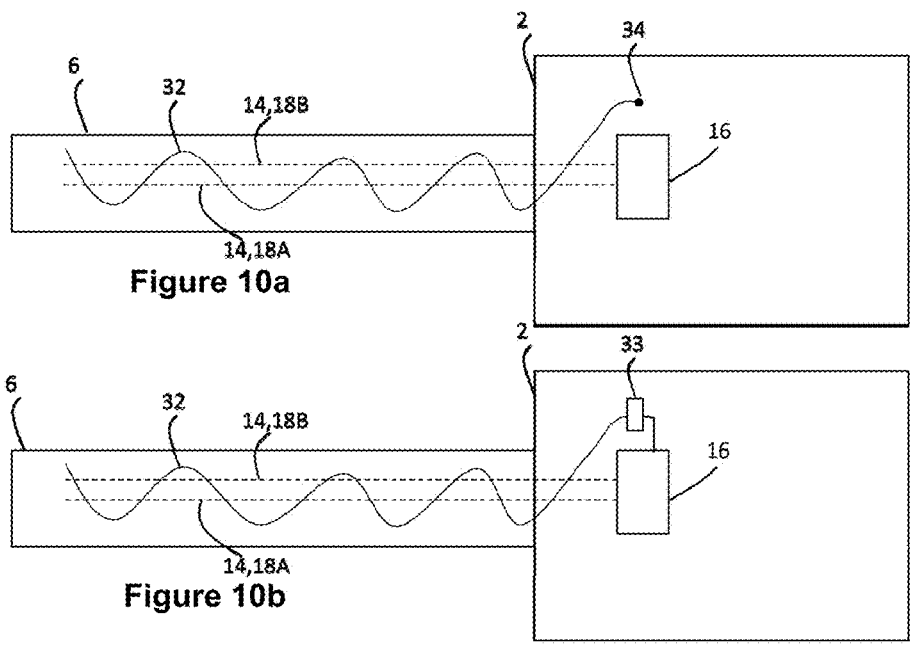
Figure 10a
Figure 10b

HEARING DEVICE INCLUDING AN EXTERNAL ANTENNA PART AND AN INTERNAL ANTENNA PART

TECHNICAL FIELD

The disclosure relates to a hearing device including a first portion adapted for being arranged behind an ear of a user, and where the first portion is coupled to a coupling element being part of an external antenna part.

BACKGROUND

Hearing aids for compensating a wearer's hearing loss are well known. The present invention is particularly related to such kinds of hearing devices. However, the present invention may also be implemented in other types of hearing devices, hearing instruments or hearing aids which comprise a connecting element between two physical parts of the device, e.g. a headset, a headphone, ear protection plugs, etc. In the following the terms "hearing device" or "hearing aid" refer to devices in general which are related to providing an acoustic signal to a user's ear.

Hearing devices, in particular hearing aids, are very dense applications, and when integrating wireless applications, it may sometimes be difficult to find sufficient space for required or desired antenna components.

It is widely known that an integration of wireless systems into hearing instruments requires integration of antenna structures as well, if bulky external antenna solutions are to be avoided. The efficiency of the antenna and the wireless system is important, as low battery consumption is commonly a design parameter. Various configurations of hearing aids as examples of hearing devices are known, such as cochlear, in-the-ear (ITE), completely-in-canal (CIC), behind-the-ear (BTE), and receiver-in-the-ear (RITE) (the latter sometimes termed 'receiver in the canal').

The efficiency and bandwidth of antennas for electromagnetic fields depend strongly on the size relative to a wavelength of the signal or field. However, common hearing instruments are typically much smaller than the wavelength in the appropriate frequency bands, which has a disadvantageous effect on the efficiency and bandwidth of the antennas build into the common hearing devices.

Additionally, an antenna of for example a RITE hearing device may comprise multiple electrically conducting elements. The electrically conducting elements being part of the antenna may have multiple other purposes, such as transmitting data and/or audio and/or power to a second portion of the hearing device or to an external part of the hearing device. In this case, each of the electrically conducting elements have to be connected to a decoupler, such as a coil, and when adding more electrically conducting elements to the antenna the bandwidth of the antenna decreases due to the decouplers connected to each of the electrically conducting elements. Furthermore, the size of the hearing device become more bulky due to the increased number of decouplers.

SUMMARY

An object of the present disclosure is to provide an antenna within a hearing device, where it is possible to increase the number of electrically conducting elements being part of the antenna and still keep the bandwidth unaffected by the number of electrically conducting elements.

A further object of the present disclosure is to provide a solution to the previous object without increasing the size of the antenna, and thereby, the size of the hearing device is more or less unaffected by the increase number of electrically conducting elements.

Objects of the present disclosure are achieved by the present disclosure described in the accompanying claims and as described in the following.

An object of the present disclosure is achieved by a hearing device comprising a first portion adapted for being arranged behind an ear of a user for providing a signal, an output transducer for converting the signal to an acoustic output, a coupling element coupled to the first portion, and wherein the coupling element is adapted for transmitting at least the signal or the acoustic output. Furthermore, the hearing device comprises an antenna which includes an external antenna part and an internal antenna part, where the internal antenna part includes a first antenna element, a second antenna element where a first end of the second antenna element is arranged at one end of the first antenna element and is connected thereto, and where a second end of the second antenna element is connected to a ground plane, and a third antenna element which is spaced at a distance from the second antenna element and connected to the first antenna element, a feeding unit configured to supply a current to the antenna via the third antenna element, a wireless interface for receiving and/or sending data by means of the antenna, and wherein the coupling element comprises the external antenna part, and where the external antenna part is connected to the internal antenna part, and wherein the coupling element comprises an electrically conducting element coupled to the wireless interface, and wherein the electrically conducting element is at least a part of the external antenna part.

A further object of the present disclosure is achieved by a hearing device comprising a first portion adapted for being arranged behind an ear of a user for providing a signal, an output transducer for converting the signal to an acoustic output, a second portion adapted for being arranged distantly from the first portion and for providing the acoustic output to the user, wherein the second portion includes the output transducer or means for bone conduction, a coupling element coupling the first portion and the second portion, and wherein the coupling element is adapted for transmitting at least the signal to the output transducer or the acoustic output to the second portion. Furthermore, the hearing device comprises an antenna which includes an external antenna part and an internal antenna part, where the internal antenna part includes a first antenna element, a second antenna element where a first end of the second antenna element is arranged at one end of the first antenna element and is connected thereto, and where a second end of the second antenna element is connected to a ground plane, and a third antenna element which is spaced at a distance from the second antenna element and connected to the first antenna element, a feeding unit configured to supply a current to the antenna via the third antenna element, a wireless interface for receiving and/or sending data by means of the antenna, and wherein the coupling element comprises an electrically conducting element coupled to the wireless interface, and wherein the electrically conducting elements is at least a part of the external antenna part, and where the electrically conducting element is connected to the first antenna element of the internal antenna part.

In the description below the internal antenna part may be referred as being an inverted-F-antenna (IF-antenna).

An object of the present disclosure is to provide an antenna within a hearing device, where it is possible to increase the number of electrically conducting elements being part of the antenna and still have a bandwidth which is suitable for communication at frequency range of about 2.45 GHz to about 5.5 GHz.

A further object of the present disclosure is to utilize a coupling element comprising an increased number of electrically conducting elements as antenna.

The internal antenna part is part of existing components of the hearing device, and the advantage of combining the internal antenna part and the external antenna part is that the decoupling of the external antenna part is not needed since the antenna current from the external antenna part is "guided" by the internal antenna part to the ground plane and not to the electrical elements within the hearing device connected to the external antenna part. Thereby, the size of the hearing device does not become bulky when adding more electrically conducting elements within the external antenna part since decouplers are not needed. Furthermore, the bandwidth of the antenna is not decreased when adding more electrically conducting elements to the antenna since the decouplers are avoided.

The hearing device may be a cochlear, in-the-ear (ITE), completely-in-canal (CIC), behind-the-ear (BTE), and receiver-in-the-ear (RITE) device.

The first portion may be arranged behind an ear of a user, such as between the pinna and the skull of the user.

The output transducer for converting the signal to an acoustic output may be part of the first portion or a second portion, wherein the second portion is connected to the first portion by the coupling element. The output transducer may be a receiver (or a speaker), or a bone anchored vibrator or cochlear.

The coupling element may be coupled to the first portion and in another example coupled to both the first portion and the second portion and/or to an external part. The coupling element may be a hollow tube comprising at least an electrically conducting element, where the electrically conducting element is configured to guide the acoustic output and/or power and/or data to the second portion and/or to the external part, where the second portion may for example be an in-the-ear canal element. The external part may comprise a transmitting coil for inductively transmitting power and/or data to an implant stimulator. The in-the-ear canal element may be formed as a dome or any shape which may improve the fitting of the second portion into an ear canal of the user.

The coupling element may comprise two or more electrically conducting elements, such as between 2 and 12, 2 and 10, or 2 and 6.

The second portion and/or the external part may include multiple sensors for acoustic signals, such as transducers, (i.e. microphone or speaker), and/or multiple sensors for monitoring the health of the user of the hearing device, where the multiple sensors may be an accelerometer, an electrode, a light emitting diode, or a photodetector. The second portion may comprise an acoustical vibrator or vibrator for bone conduction.

The second portion and/or the external part may include a memory and a processor for controlling the sensors and/or processing signals to be detected or transmitted by the sensors.

The advantage of being able to provide multiple electrically conducting elements within the coupling element is that the second portion and the external part becomes more intelligent than today's solutions and which results in an improved comfort for the user.

Further advantage is that the size of the first portion can be reduced by providing more features into the second portion and/or the external part due to the availability of including more electrically conducting elements into the coupling element without affecting the bandwidth due to an internal parasitic element.

The second portion may be adapted to be arranged distantly from the first portion and in proximity to a skin of the user.

The coupling element may comprise an inner core and an outer core, where the outer core encircles the inner core. The inner core may comprise air configured to guide the acoustic output and the outer core may comprise the external antenna part in the form of electrically conducting element(s).

The coupling element may comprise a core, where the core may include the external antenna part in the form of electrically conducting element(s).

The coupling element connected to the first portion may be an earhook firmly attached to the first portion of the hearing device. The coupling element may be configured for mechanical detachment, allowing the earhook to be easily replaced should the earhook antenna element malfunction, or if an alternative earhook is desired.

The hearing device may comprise at least two coupling elements, where a first coupling element may be coupled to the first portion, or the first coupling element may be coupled to the first portion and the second portion. A second coupling element may be coupled to the first portion and the external part. The external part may comprise a transmitting coil for inductively transmitting power and/or data to an implant stimulator. Both coupling elements comprise electrical conducting element(s) where the external antenna part may be part of both coupling elements or one of the coupling elements. In the example where the external antenna part is part of both coupling elements, a first coupling element may comprise a first group of electrically conducting element, and a first external antenna part may be part of the first group of electrically conducting element. The second coupling element may comprise a second group of electrically conducting element, and a second external antenna part may be part of the second group of the electrically conducting element.

Having multiple coupling elements results in a reduced size of the first portion since the technical features of the first portion can be transferred to both the second portion and/or the external part due to the possibility of implementing more electrically conducting elements into the coupling element(s). Additionally, the advantage of having two coupling elements is that the hearing device can communicate to other external devices via multiple different or similar wireless communication protocol links with minimal interference between the two links. The interference between the two links is minimal since the distance between the coupling element is much larger than if they were inside the first portion. The multiple coupling elements may comprise a first coupling element and a second coupling element. The first coupling element may comprise a first group of electrically conducting elements and the second coupling element may comprise a second group of electrically conducting elements. The first group of electrically conducting elements may be connected to a first wireless interface configured to communicate Bluetooth at about 2.45 GHz, and the second group of electrically conducting elements may be connected to a second wireless interface configured to communicate a second protocol at a different frequency, such as about 900 MHz or about 5.3 GHz. The first and the second wireless interface may be within the first portion.

It is important to understand that the main part of the external antenna part is positioned outside the first portion. The external antenna part may be an electrically conducting element, such as a wire or a flexible printed circuit board element. The electrically conducting element may be connected to the wireless interface and terminated within the coupling element and/or within the second portion and/or within the external part.

The external antenna part may at least be adapted for carrying the signal upon transmission to the output transducer The external antenna part may be partly within the first portion and partly outside the first portion. The part which is within the first portion is connected to the wireless interface and the internal antenna part.

The internal antenna part may include a first antenna element, a second antenna element where a first end of the second antenna element may be arranged at one end of the first antenna element and is connected thereto, and where a second end of the second antenna element may be connected to the ground plane, and a third antenna element which is spaced at a distance from the second antenna element and connected to the first antenna element. The first antenna element may be horizontally oriented in view of the second antenna element and the third antenna element forming an inverted-F antenna. The electrical length of the first antenna element is $\lambda/4$ or $\lambda/4+x*\lambda/2$, where x is a number, such as 0, 1, 2, 3 etc.

The internal antenna part may be formed by a conducting plate, and/or an electrically conducting path wire and/or a flexible print.

The internal antenna part, i.e. the first antenna element, the second antenna element and the third antenna element, may be formed by an electrically conducting path mounted on a conducting plate, where the electrically conducting path is connected to the electrically conducting element of the external antenna part. The electrically conducting path may further be connected to the ground plane.

Additional, the internal antenna part may comprises multiple electrically conducting paths and the external antenna part may comprise multiple electrically conducting elements, wherein each of the conducting paths are connected to an electrically conducting elements. The connection between each of the electrically conducting paths and the electrically conducting elements may be provided via a capacitor. The capacitor provides an efficient coupling between the internal antenna part and the external antenna part, such as an efficient coupling which makes sure that the external antenna part receives the current from the feeding unit and that the antenna current from the external antenna part is transferred to the ground plane. Thereby, no decoupler is needed to be coupled to each of the electrically conducting elements.

In an alternative solution, when having multiple electrically conducting elements, at least one of the multiple electrically conducting elements may be coupled to an electrically conducting path of the internal antenna part. In this solution the other electrically conducting elements, i.e. the electrically conducting elements which are not coupled to an electrically conducting path (or to the internal element), may any way receive the current from the feeding unit via magnetic coupling and/or capacitive coupling from the one electrically conducting element which is connected to the electrically conducting path (or to the internal element). Additional, the advantage of this solution is that only a single capacitor is needed in order to have an efficient coupling between the internal antenna part and the external antenna part.

A further advantage of this solution is that the size of the antenna (i.e. the hearing device) is minimal affected when adding more electrically conducting elements to the external antenna part since you are avoiding decouplers and the number of capacitor is reduced significantly.

The distance between the third antenna element and the second antenna element is determined based on the ratio between the current of the current distribution and the voltage of the voltage distribution along the first antenna element. The ratio should be 50 ohm.

The position of the connection point of the feeding unit on to the internal antenna part is determined by the current and/or the voltage distribution along the first antenna element. Ideally, the position of the connection point should be where the ratio between voltage and current is 50 ohm.

The second antenna element may be connected to the ground plane. The electrical length of the ground plane may be $\lambda/4$ or $\lambda/4+x*\lambda/2$, where x is a number, such as 0, 1, 2, 3 etc. The second antenna element may be an electrically conducting element, such as a wire or a flexible printed circuit board element The internal antenna part may comprise a fourth antenna element and a fifth antenna element, where a first end of the fifth antenna element may be arranged at one end of the fourth antenna element and is connected thereto, and where a second end of the fifth antenna element may be connected to the first antenna element, and where the fourth antenna element may be partly parallel with the first antenna element, and where the electrical length of the fourth antenna element may be larger than the electrical length of the first antenna element.

The advantage of the fourth antenna element and the fifth antenna element is that the antenna is configured to operate at multiple frequency within multiple frequency ranges. In one specific embodiment, the antenna may be configured to communicate with multiple external devices using two communication protocol links, where the frequency of both links are within a frequency range of about 2.45 GHz to about 5.5 GHz, or between 2.44 GHz to 5.5 GHz or about the frequency of 2.45 GHz or about the frequency of 5.5 GHz.

The antenna may comprise an internal parasitic element, and where the feeding unit is further configured to supply the current to the internal parasitic element via a wireless coupling, such as a magnetic coupling or a capacitive coupling.

The advantage of combining the external antenna part and the parasitic element is that the bandwidth of the antenna increases and that the obtained improvement of the bandwidth is obtained by not increasing the size of the hearing device.

The internal parasitic element is preferably arranged within the first portion, however, the internal parasitic element may in another example of the present disclosure be arranged within the external part and/or within the second portion and/or within the coupling element.

The internal parasitic element may be supplied with current from the feeding unit via magnetic coupling and/or capacitive coupling. It is important to understand that the present disclosure does not include a solution where the internal parasitic element receives a current via a galvanic coupling or via a printed circuit board.

The internal parasitic element may be part of the printed circuit board connected to a ground plane such that the internal parasitic element only receives a current via the magnetic coupling or via the capacitive coupling. The current from the feeding unit may be transferred via the ground plane and/or via the external antenna part and wireless coupled to the internal parasitic element.

The internal parasitic element may be a passive element being electrically conductive and connected to the ground plane.

An electrical length of the internal parasitic element may be $\lambda/4$ or $\lambda/4+x*\lambda/2$, where x is a number, such as 0, 1, 2, 3 etc. The electrical length of the internal parasitic element may be adapted to the ground plane and/or the external antenna part. The electrical length may be any length, and where the impedance match between the internal parasitic element and the external antenna is obtained by an impedance matching circuit. The impedance matching circuit may comprise one or more capacitance and/or one or more coils. The impedance matching circuit may be connected to the internal parasitic element and ground plane or between the external antenna and the ground plane.

The antenna may be connected to a wireless interface being configured to transmit and/or receive audio or data. The wireless interface may be part of a printed circuit board. The wireless interface may be adapted for receiving and/or transmitting audio or data by electromagnetic radiation in the frequency range of about 2.45 GHz to about 5.5 GHz, or between 2.44 GHz to 5.5 GHz or about the frequency of 2.45 GHz or about the frequency of 5.5 GHz.

The hearing device may comprise a second portion and/or an external part adapted for being arranged distantly from the first portion and for providing the acoustic output to the user, and wherein the coupling element is configured to couple the first portion and the second portion and/or the external part, and wherein the coupling element is adapted for transmitting at least the signal to the output transducer which is within the second portion, and/or transmitting at least the signal to the external part, and/or transmitting the acoustic output, provided by the output transducer which is positioned within the first portion, to the second portion, and wherein the coupling element comprises an electrically conducting element coupled to the wireless interface, and wherein the electrically conducting element is at least a part of the external antenna part, and where the electrically conducting element is connected to the internal antenna part.

The second portion is arranged in an ear canal of the user, and/or the external part may be arranged on a skin part of the user (including the skull of the user).

The current within the feeding unit is mainly magnetically coupled to the internal parasitic element. This solution provides a more compact antenna where the inner part of the external antenna part and the internal parasitic element are positioned close together. The transfer of the current between the feeding unit and the internal parasitic element may comprise capacitive coupling.

Additionally, at least a part of the external antenna part and the internal parasitic element may be arranged within the first portion such that a capacitive coupling is provided between the internal parasitic element and/or the external antenna part and/or the internal antenna part. The capacitive coupling improves the production tolerance of antenna.

The antenna may comprise a ground plane guiding the current from the feeding unit along a length of the ground plane, and wherein the internal parasitic element is positioned within the hearing device such that the current guided by the ground plane is coupled magnetically to the internal parasitic element. By having the ground plane the internal parasitic element can be positioned further away as compared to the previous antenna solution where the internal parasitic element receives the current directly via the wireless coupling to the feeding unit.

The coupling element may comprise one or more shield elements for shielding the external antenna part such that electrical elements within the first portion, the second portion, the external part and/or external devices will not be affected negatively by radiation from the antenna which has a frequency outside the frequency range of about 2.45 GHz to about 5.5 GHz, or between 2.44 GHz to 5.5 GHz or about the frequency of 2.45 GHz or about the frequency of 5.5 GHz.

The external device may be a cellphone, a computer or any electronic devices which is not part of the hearing device.

The shield element may be connected to the wireless interface via a bandpass filter, or the shield element may be connected to the ground plane within the first portion.

The shield element may be a wire twisted around the electrically conductive elements or a net of wires twisted around the electrically conductive elements. The coupling element may comprise a first group of electrically conductive elements and a second group of electrically conductive elements (and multiple other groups of electrically conductive elements). A first shield element may cover the first group and a second shield element may cover the second group, and thereby, we avoid any disturbance which may occur between the groups of electrically conductive elements. For example, the first group may be connected to a microphone and the second group may be connected to a speaker.

The feeding unit may be configured to supply the current to the second antenna being at least part of the antenna, and wherein the external antenna part and the second antenna are electrically coupled together by a capacitive coupling or a magnetic coupling so that the second antenna is able to extend the operation of the external antenna part.

The second antenna may be within the first portion connected to the wireless interface and another electrical element within the first portion.

The second antenna may be an electrically conducting element, such as a wire or a flexible printed circuit board element.

A method for a wireless receiving and/or sending of data in a hearing device comprising an output transducer, a coupling element coupling a first portion of the hearing device, the first portion providing a signal and the output transducer is configured to convert the signal to an acoustic output, the method comprising the steps of:

providing an external antenna part within the coupling element, providing an internal antenna part, where the internal antenna part includes a first antenna element, a second antenna element where a first end of the second antenna element is arranged at one end of the first antenna element and is connected thereto, and where a second end of the second antenna element is connected to a ground element, and a third antenna element which is spaced at a distance from the second antenna element and connected to the first antenna element, connecting the internal antenna part to the external antenna part, supplying a current to the electrically conducting element by a feeding unit and via the internal antenna part, arranging the first portion behind an ear of a user of the hearing aid, and receiving and/or sending data by means of the antenna.

A method for a wireless receiving and/or sending of data in a hearing device comprising a coupling element coupling a first portion and a second portion of the hearing device, the first portion providing a signal and the second portion comprising an output transducer for converting the signal to an acoustic output, the method comprising the steps of:
- providing an electrically conducting element in the coupling element where the electrically conducting element is at least part of an external antenna part,
- providing an internal antenna part, where the internal antenna part includes a first antenna element, a second antenna element where a first end of the second antenna element is arranged at one end of the first antenna element and is connected thereto, and where a second end of the second antenna element is connected to a ground element, and a third antenna element which is spaced at a specific distance from the second antenna element and connected to the first antenna element,
- connecting the internal antenna part to the external antenna part,
- supplying a current to the electrically conducting element by a feeding unit and via the internal antenna part,
- arranging the first portion behind an ear of a user of the hearing aid,
- arranging the second portion in an ear canal of the user or on a skin of the user, and
- receiving and/or sending data by means of the electrically conducting element.

A hearing device comprising a first portion adapted for being arranged behind an ear of a user for providing a signal, an output transducer for converting the signal to an acoustic output, a coupling element coupled to the first portion, and wherein the coupling element is adapted for transmitting at least the signal or the acoustic output, an antenna comprising an external antenna part and an internal antenna part, where the internal antenna part includes a first antenna element, a second antenna element, where a first end of the second antenna element is arranged at one end of the first antenna element and is connected thereto, and where a second end of the second antenna element is connected to a ground plane, and a third antenna element which is spaced at a distance from the second antenna element and connected to the first antenna element, a feeding unit configured to supply a current to the antenna via the third antenna element, a wireless interface for receiving and/or sending data by means of the antenna, and wherein the coupling element comprises the external antenna part, and where the external antenna part is connected to the internal antenna part, and wherein the coupling element comprises an electrically conducting element coupled to the wireless interface, and wherein the electrically conducting element is at least a part of the external antenna part.

The hearing device may comprise a second portion adapted for being arranged distantly from the first portion and for providing the acoustic output to the user, and wherein the coupling element coupling the first portion and the second portion, and wherein the coupling element is adapted for transmitting at least the signal and/or the acoustic output.

The hearing device may comprise an external part being arranged distantly to the first portion, and wherein the external part includes an implant stimulator where the coupling element or a second coupling element is coupling the first portion and the external part, and wherein the coupling element or the second coupling element is adapted for transmitting at least the signal, and wherein the second coupling element comprises an electrically conducting element coupled to the wireless interface, and wherein the electrically conducting element is at least a part of the external antenna part.

The second portion may be arranged in an ear canal of the user, and wherein the second portion includes the output transducer, and/or the external part is arranged on a skin part of the user.

The first antenna element, the second antenna element and the third antenna element may be formed by an electrically conducting path mounted on a conducting plate, where the electrically conducting path is connected to the electrically conducting element of the external antenna part.

The distance between the third antenna element and the second antenna element is determined based on the ratio between the voltage of a voltage distribution and a current of a current distribution along the first antenna element and the second antenna element.

An electrical length of the first antenna element, the second antenna element and the external antenna part may be in total $\lambda/4$ or $\lambda/4+x*\lambda/2$, where x is a number, such as 0, 1, 2, 3 etc., or the electrical length of the first antenna element, the second antenna element and the electrically conducting element(s) is in total $\lambda/4$ or $x*\lambda/4+/-\lambda/2$, where x is an odd number such as 3, 5, 7 etc.

An electrical length of the ground plane may be $\lambda/4$ or $\lambda/4+x*\lambda/2$, where x is a number, such as 0, 1, 2, 3 etc.

The internal antenna part may comprise a fourth antenna element and a fifth antenna element, where a first end of the fifth antenna element is arranged at one end of the fourth antenna element and is connected thereto, and where a second end of the fifth antenna element is connected to the first antenna element, and where the fourth antenna element is partly parallel with the first antenna element, and where the electrical length of the fourth antenna element is larger than the electrical length of the first antenna element.

The antenna may comprise an internal parasitic element, and where the feeding unit is further configured to supply the current to the internal parasitic element via a wireless coupling, such as a magnetic coupling or a capacitive coupling.

The current within the feeding unit may be magnetically and/or capacitive coupled to the internal parasitic element.

The ground plane may be guiding the current from the feeding unit along a length of the ground plane, and wherein the internal parasitic element is positioned within the hearing device such that the current guided by the ground plane is coupled magnetically and/or capacitive to the internal parasitic element.

An electrical length of the internal parasitic element may be $\lambda/4$ or $\lambda/4+x*\lambda/2$, where x is a number, such as 0, 1, 2, 3 etc.

The internal parasitic element may be positioned such that a capacitive coupling is provided between the internal parasitic element and the external antenna part, where the capacitive coupling comprises a current being transferred from the external antenna part to the parasitic element.

The electrically conducting element may be at least adapted for carrying the signal upon transmission to the output transducer.

The external antenna part may comprise multiple electrically conducting elements, where two or more electrically conducting elements are connected to one or more electronic devices mounted within the second portion or the external part of the hearing device, and where each of the electrically conducting elements are at least adapted for carrying a signal provided by the first portion to the connected electronic device.

The two or more electrically conducting elements may be terminated within the second portion or within the coupling element, external part or within the coupling element (or within the second coupling element).

The electronic device(s) within the second portion is a transducer, such as another output transducer or a microphone, and/or a sensor, and/or a light emitting diode and/or an electrode and/or a photodetector.

The wireless interface may be adapted for receiving and/or sending data by electromagnetic radiation in the frequency range of about 2.45 GHz to about 5.5 GHz, or between 2.44 GHz to 5.5 GHz or about the frequency of 2.45 GHz or about the frequency of 5.5 GHz.

The coupling element may comprise one or more shield elements for shielding the external antenna part.

The shield element may be connected to the wireless interface via a bandpass filter, or the shield element is connected to a ground element within the first portion.

The feeding unit may be configured to supply the current to a second antenna being at least part of the antenna, and wherein the external antenna part and the second antenna are electrically coupled together by a capacitive coupling or a magnetic coupling so that the second antenna is able to extend the operation of the external antenna part.

A method for a wireless receiving and/or sending of data in a hearing device comprising an output transducer, a coupling element coupling a first portion of the hearing device, the first portion providing a signal and the output transducer is configured to convert the signal to an acoustic output, the method comprising the steps of:
 providing an external antenna part within the coupling element, where the external antenna part is part of an antenna,
 providing an internal antenna part being part of the antenna, where the internal antenna part includes a first antenna element, a second antenna element where a first end of the second antenna element is arranged at one end of the first antenna element and is connected thereto, and where a second end of the second antenna element is connected to a ground element, and a third antenna element which is spaced at a distance from the second antenna element and connected to the first antenna element,
 connecting the internal antenna part to the external antenna part,
 supplying a current to the external antenna part by a feeding unit and via the internal antenna part,
 arranging the first portion behind an ear of a user of the hearing aid, and receiving and/or sending data by the antenna.

An external antenna is similar to the external antenna part.

A hearing device may comprise a first portion adapted for being arranged behind an ear of a user for providing a signal, an output transducer for converting the signal to an acoustic output, a coupling element coupling to the first portion, an antenna comprising an external antenna arranged at least externally to the first portion and an internal parasitic element, a feeding unit configured to supply a current to the external antenna, and the feeding unit is further configured to supply the current to the internal parasitic element via a wireless coupling, a wireless interface for receiving and/or transmitting data by means of the antenna, and wherein the coupling element comprises the external antenna, and wherein the coupling element comprises an electrically conducting element coupled to the wireless interface, and wherein the electrically conducting element is at least a part of the external antenna.

The hearing device may comprise a second portion adapted for being arranged distantly from the first portion and for providing the acoustic output to the user, and wherein the coupling element coupling the first portion and the second portion, and wherein the coupling element is adapted for transmitting at least the signal and/or the acoustic output.

The hearing device may comprise an external part being arranged distantly to the first portion, and wherein the external part includes an implant stimulator where the coupling element or a second coupling element is coupling the first portion and the external part, and wherein the coupling element or the second coupling element is adapted for transmitting at least the signal, and wherein the second coupling element comprises an electrically conducting element coupled to the wireless interface, and wherein the electrically conducting element is at least a part of the external antenna.

The second portion is arranged in an ear canal of the user, and wherein the second portion includes the output transducer, and/or the external part is arranged on a skin part of the user. The current within the feeding unit may be magnetically coupled to the internal parasitic element.

The antenna may comprise a ground plane guiding the current from the feeding unit along a length of the ground plane, and wherein the internal parasitic element is positioned within the hearing device such that the current guided by the ground plane is coupled magnetically to the internal parasitic element.

An electrical length of the internal parasitic element may be $\lambda/4$ or $\lambda/4+x*\lambda/2$, where x is a number, such as 0, 1, 2, 3 etc.

At least a part of the external antenna may be arranged within the first portion and the internal parasitic element is positioned such that a capacitive coupling is provided between the internal parasitic element and the external antenna.

The second portion may comprise the output transducer, and wherein the external antenna element is at least adapted for carrying the signal upon transmission to the output transducer.

The external antenna may comprise multiple electrically conducting elements, where two or more electrically conducting elements are connected to one or more electronic devices mounted within the second portion of the hearing device, and where each of the electrically conducting elements are at least adapted for carrying a signal provided by the first portion to the electronic devices within the second portion.

The two or more electrically conducting elements may be terminated within the second portion, external part or within the coupling element (or within the second coupling element).

The electronic device(s) within the second portion may be a transducer, such as another output transducer or a microphone, and/or an accelerometer, an electrode, a light emitting diode, and/or a photodetector.

The wireless interface is adapted for receiving and/or transmitting data by electromagnetic radiation in the frequency range of about 2.45 GHz to about 5.5 GHz, or between 2.44 GHz to 5.5 GHz or about the frequency of 2.45 GHz or about the frequency of 5.5 GHz.

The coupling element may comprise one or more shield elements for shielding the external antenna.

The shield element may be connected to the wireless interface via a bandpass filter, or the shield element is connected to a ground plane within the first portion.

The feeding unit may be configured to supply the current to a second antenna being at least part of the antenna, and wherein the external antenna and the second antenna are electrically coupled together by a capacitive coupling or a magnetic coupling so that the second antenna is able to extend the operation of the external antenna.

A method for a wireless receiving and/or transmitting of data in a hearing device comprising a coupling element coupling to a first portion, where the first portion providing a signal, and an output transducer for converting the signal to an acoustic output, the method comprising the steps of:
providing an external antenna in the coupling element and at least externally to the first portion,
supplying a current to the external antenna by a feeding unit,
providing an internal parasitic element internally in the first portion,
supplying the current to the internal parasitic element via wireless coupling,
arranging the first portion behind an ear of a user of the hearing aid, and
receiving and/or transmitting data by means of the external antenna.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 9, illustrates an example of the hearing device including a shield element, FIGS. 10a-10b, illustrate an example of the hearing device including a shield element.

DETAILED DESCRIPTION

Figure 1A:
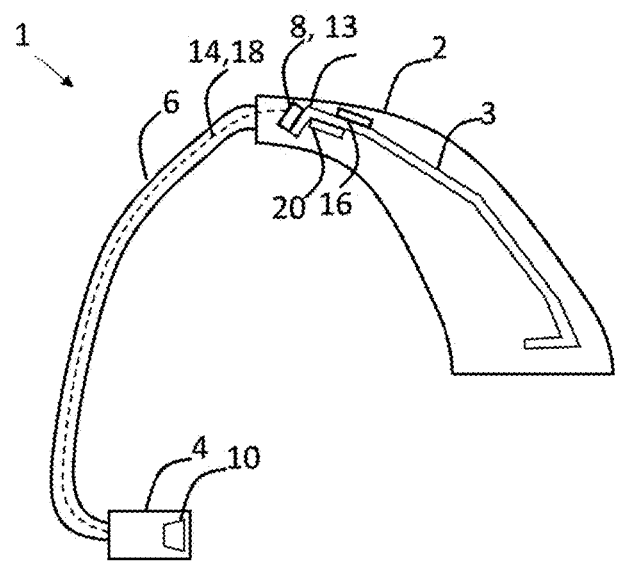
FIGS. 1a-1c, illustrate an example of a hearing device and an example of the antenna within the hearing device.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals or with a receiver/loudspeaker arranged close to or in the ear canal such as in a Behind-the-Ear type hearing aid or a Receiver-in-the Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A hearing device may be part of a "hearing system", which refers to a system comprising one or two hearing devices, disclosed in present description, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefiting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follows.

Figures 1B, 1C:
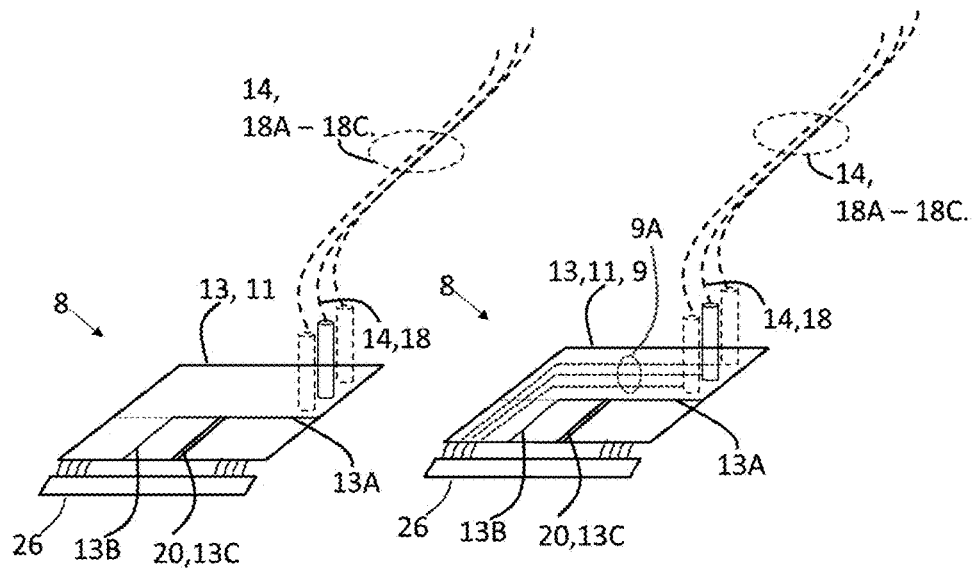

FIG. 1a-1c an example of a hearing device 1 and an example of the antenna 8 within the hearing device 1. FIG. 1a shows a hearing device 1 comprising a first portion 2 adapted for being arranged behind an ear of a user for providing a signal, an output transducer 10 for converting the signal to an acoustic output, a coupling element 6 coupling to the first portion 2, an antenna 8 comprising an external antenna part 14 arranged at least externally to the first portion 2 and an internal antenna part 13 arranged within the first portion, a feeding unit 20 configured to supply a current to the external antenna part 14 via the internal antenna part 13. The hearing device 1 further comprises a wireless interface 16 configured to receive and/or send data and/or audio and/or power by means of the antenna. The coupling element 6 comprises the external antenna part 14, and the external antenna part 14 is connected to the internal antenna part 13. In this specific example, the hearing device 1 further comprises a second portion 4 adapted for being arranged distantly from the first portion 2 and for providing the acoustic output to the user, where the second portion 4 includes the output transducer 10. The coupling element 6 is coupling the first portion 2 and the second portion 4, and wherein the coupling element 6 is adapted for transmitting at least the signal to the output transducer 10, and wherein the coupling element 6 comprises an electrically conducting element 18 coupled to the wireless interface 16, and wherein the electrically conducting elements 18 is at least a part of the external antenna part 14.

FIG. 1b illustrates the antenna 8 including the internal antenna part 13 being part of a main plane 11 and the electrically conducting elements 18A-18C which are at least part of the external antenna part 14. In this specific example, the internal antenna part 13 comprises a first antenna element 13A, a second antenna element 13B where a first end of the second antenna element 13B is arranged at one end of the first antenna element 13A and is connected thereto, and where a second end of the second antenna element 13B is connected to a ground plane 26, and a third antenna element 13C which is spaced apart from the second antenna element 13B and connected to the first antenna element 13A. The electrically conducting elements 18A-18C are connected to the internal antenna part 13 via the first antenna element 13A.

FIG. 1c illustrates the antenna 8 of the hearing device 1, were the second antenna element 13B and the third antenna element 13C are formed by one or more electrically conducting paths 9A in the main plane 11, where the electrically conducting paths 9A of the internal antenna part are connected to the electrically conducting elements 18A-18C of the external antenna part 14. In this specific example the electrically conducting paths 9A are mounted on a conducting plate 9.

Figure 2:
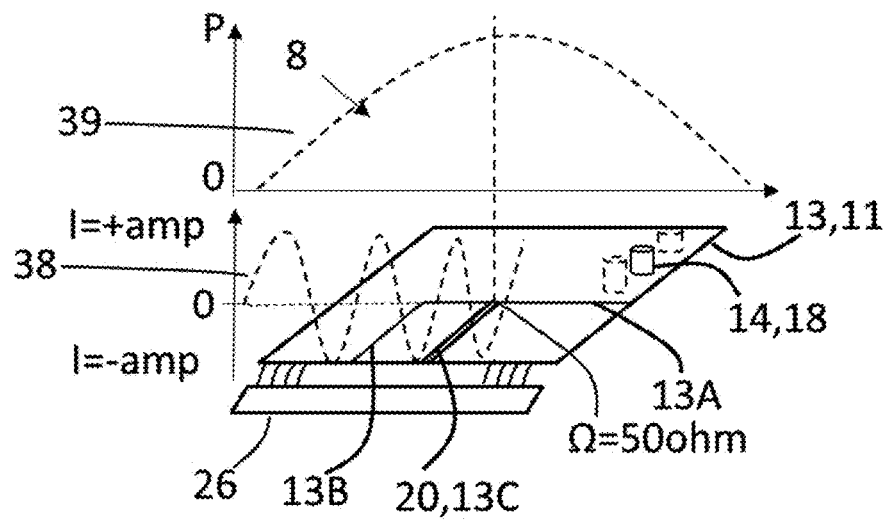
FIG. 2, illustrates an example of the antenna within the hearing device.

FIG. 2 illustrates that the distance between the second antenna element 13B and the third antenna element 13C is determined based on the ratio between the voltage of the voltage distribution 39 and the current of the current distribution 38 along the first antenna element 13A. In this specific example, the position of the connection point of the feeding unit 20 to the internal antenna part 13 is where the ratio between the voltage and the current is 50 ohm.

Figure 3:
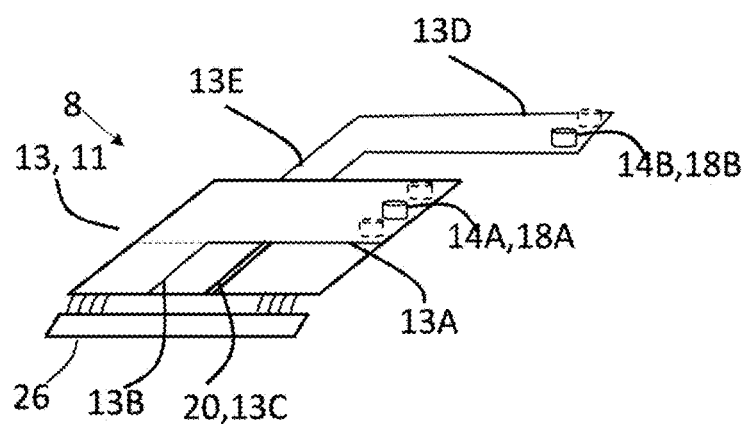

FIG. 3 illustrates the antenna 8 where the internal antenna part comprises a fourth antenna element 13D and a fifth antenna element 13E, where a first end of the fifth antenna element 13E is arranged at one end of the fourth antenna element 13D and is connected thereto, and where a second end of the fifth antenna element 13E is connected to the first antenna element 13A, and where the fourth antenna element 13D is partly parallel with the first antenna element 13A, and where the electrical length of the fourth antenna element 13D is larger than the electrical length of the first antenna element 13A.

In this specific example the internal antenna part 13 is a dual band inverted F antenna having at least two frequency, i.e. operating frequency, where a first frequency is represented by the fourth and the fifth antenna element (13D, 13E), and a second frequency is represented by the remaining antenna element (13A-13C) of the internal antenna part 13. If the fourth antenna element 13D has a longer electrical length than the first antenna element 13A results in that the first frequency is less than the second frequency.

Figure 4A:
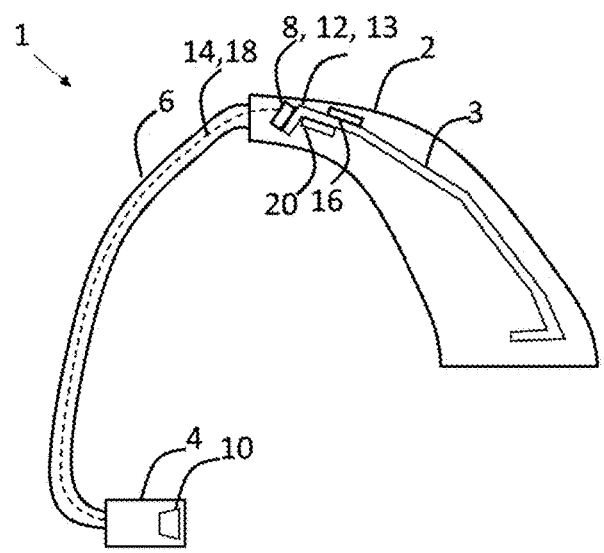
FIGS. 4a-4b, illustrate a further example of the hearing device including an internal parasitic element.
Figure 4B:
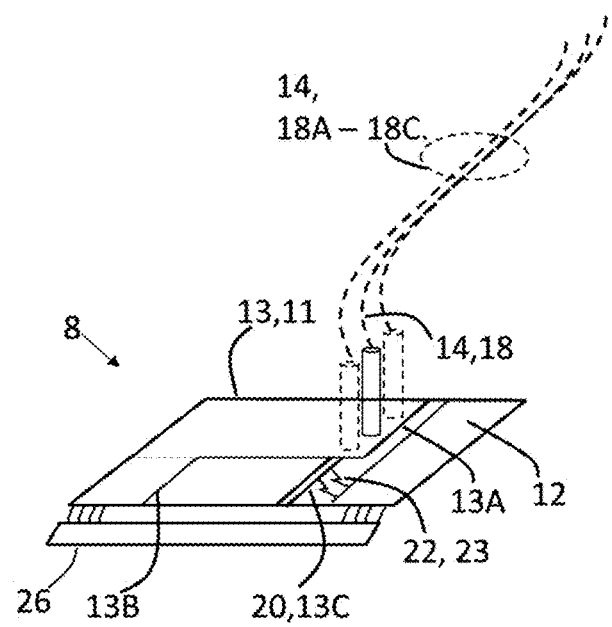

FIG. 4a-4b illustrate the hearing device 1 where the antenna 8 comprises an internal parasitic element 12, the internal antenna part 13 and the external antenna part (14, 18). FIG. 4a illustrates a similar hearing device as described in FIG. 1a, however, in this specific example, the hearing device comprises the internal parasitic element 12. FIG. 4b illustrates the antenna 8 including the internal parasitic element 12. In this specific example, the feeding unit is positioned such that a current is supplied to the internal parasitic element via a wireless coupling, such as a magnetic coupling 22 and/or a capacitive coupling 23. The internal parasitic element 12 is connected to the ground plane 26.

Figure 5A:
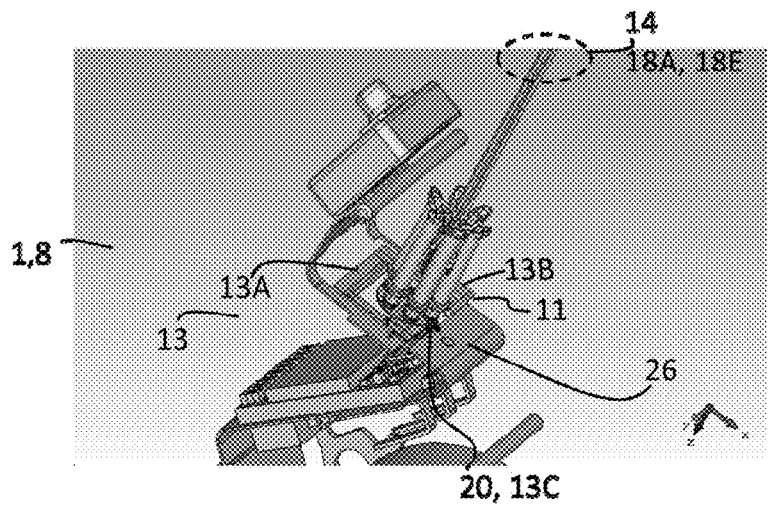
FIGS. 5a-5c, illustrate an example of the hearing device and a simulation of the resonance frequency.
Figure 5B:
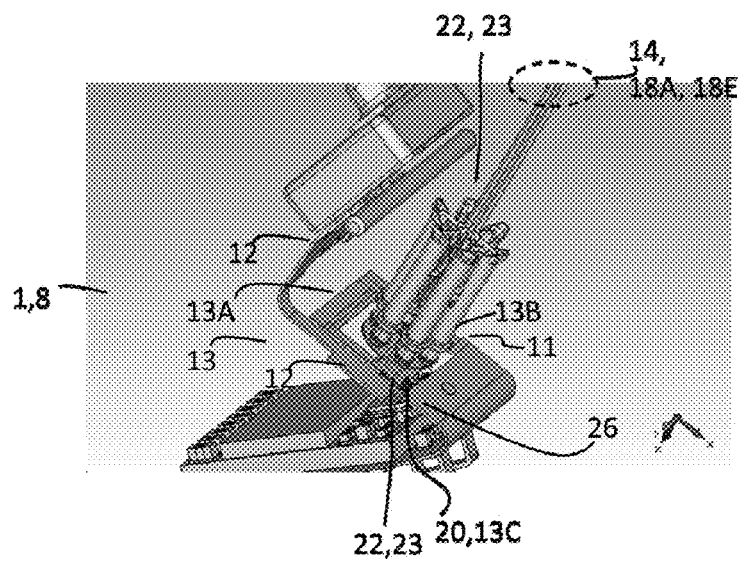
Figure 5C:
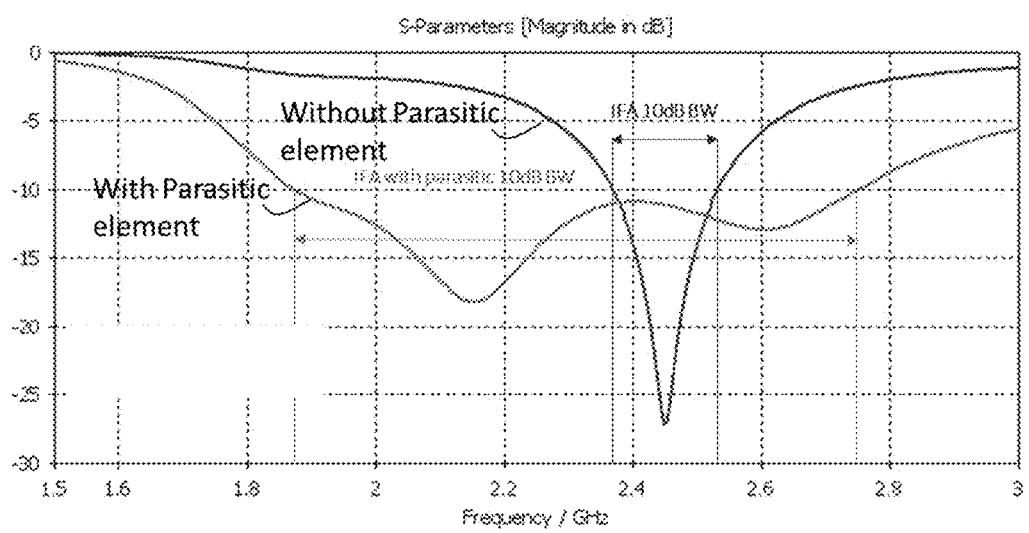

FIGS. 5a-5c illustrate a simulation of the hearing device 1 with and without the internal parasitic element 12. FIG. 5a illustrates the hearing device 1 without the internal parasitic element 12, and FIG. 5b illustrates the hearing device 1 with the internal parasitic element, and FIG. 5c illustrates the simulation result of the hearing device 1 with and without the internal parasitic element 12. The result shows that the 10 dB bandwidth of the antenna without the internal parasitic element 12 is less than the 10 dB bandwidth of the antenna 8 with the internal parasitic element 12. This clearly shows that the solution with multiple electrically conductive elements 18A-18E, acting as the external antenna part 14, has an improved bandwidth when including the parasitic element 12 into the design of the antenna 8.

Figures 6A, 6B:
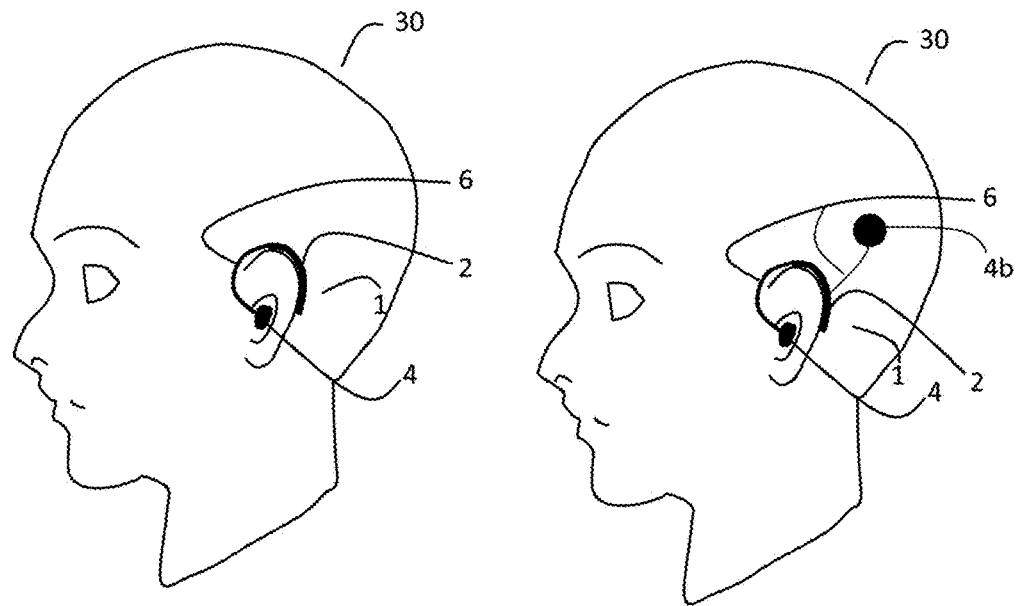
FIGS. 6a-6d, illustrate different examples of the hearing device.
Figures 6C, 6D:
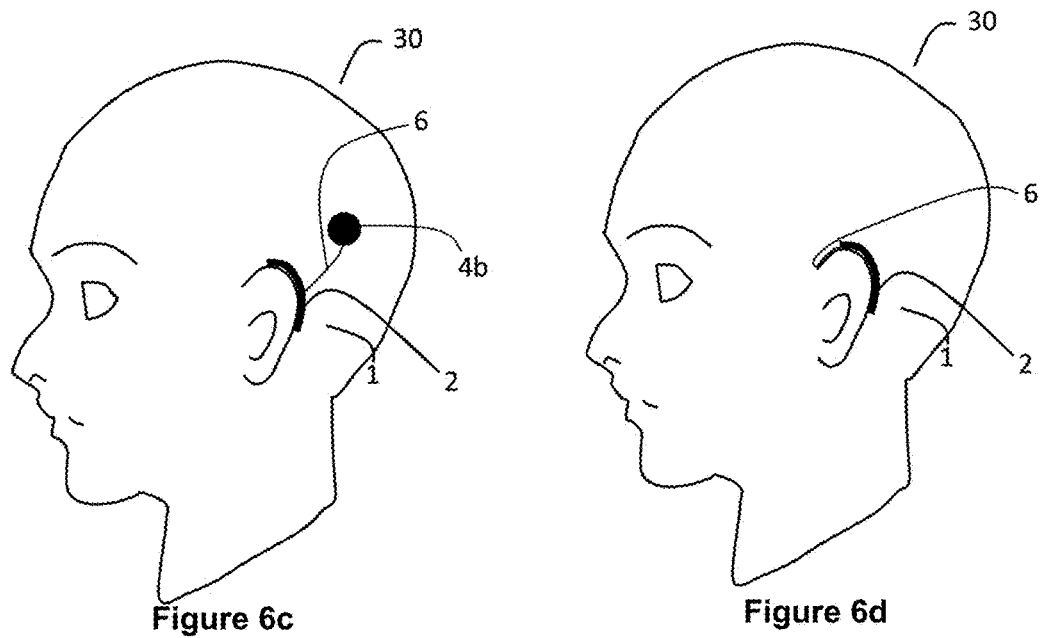

FIGS. 6a-6d illustrate the hearing device 1 worn by a user 30. FIG. 6a illustrates a behind-the ear hearing aid 1, where the first portion 2 is positioned between the pinna of the ear of the user 30 and the skull of the user 30. The second portion 4 is positioned within the ear canal of the user 30. The first portion 2 and the second portion 4 are coupled via a coupling element 6. The coupling element 7 may be configured to transfer the acoustic output via air or configured to transfer the signal via the electrically conducting element 18. FIG. 6b illustrates a cochlear hearing aid 1 where the first portion 2 is connected 6 to both the second portion 4 and an external part 4b, where the external part 6 is an implant stimulator. The connection 6 comprises a first and a second coupling element, where the first and the second coupling element may be similar to the coupling element described previously. FIG. 6c illustrates a cochlear hearing aid 1 where the first portion 2 is connected 6 to the external part 4b via the coupling element 6. FIG. 6d illustrates a hearing device 1 where the coupling element 6 is an earhook 6 detachable mounted to the first portion 2.

Figure 7:
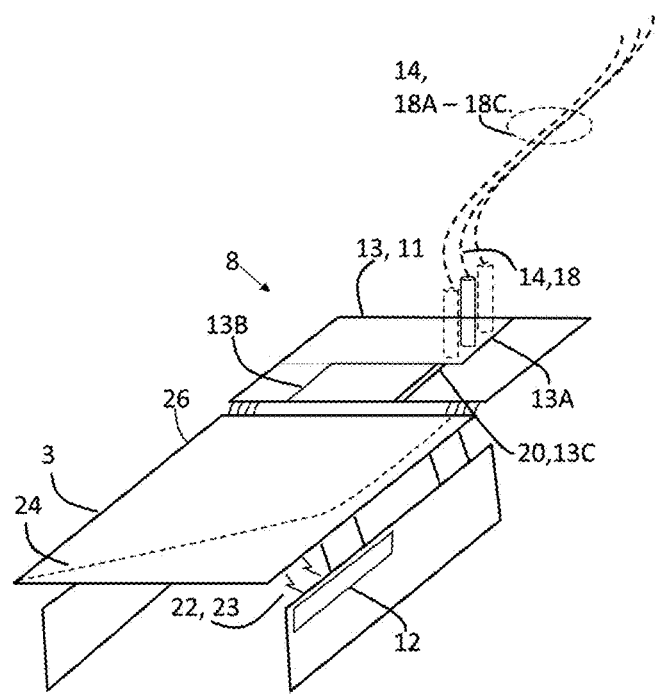
FIG. 7, illustrates a further example of the hearing device including an internal parasitic element.

FIG. 7 illustrates the antenna 8 where the internal parasitic element is not part of the main plane 11 but instead is mounted distantly from the external antenna part 14, for example on a Printed Circuit Board (PCB) 3 within the first portion 2. The internal parasitic element 12 receives the current 24 from the feeding unit 20 via a wireless coupling (22, 23) between the ground plane 26 and the internal parasitic element 12.

Figure 8:
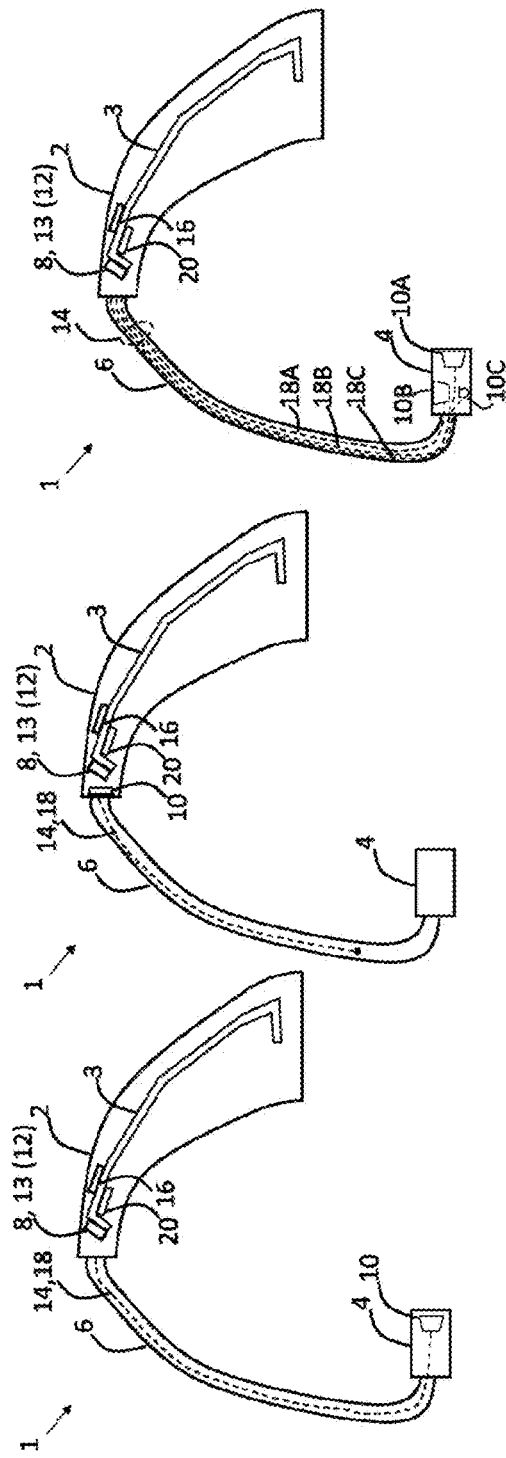
FIGS. 8a-8c, illustrate different example of the hearing device.

FIGS. 8a-8c illustrate multiple different examples of the hearing device 1, where the coupling element 6 is either a hollow tube including one or more electrically conductive elements or a hollow tube including an inner core and outer core, where the outer core encircles the inner core. The inner core may comprise air configured to guide the acoustic output and the outer core may comprise the electrically conducting element(s) 18, i.e. the external antenna part 14. FIG. 8a illustrates that the electrically conductive elements 18 are terminated within the second portion 4 and connected to an output transducer 10. FIG. 8b illustrates that the electrically conductive elements 18 are terminated within the coupling element 6. The first portion comprises the output transducer. FIG. 8c illustrates multiple electrically conductive elements (18A-18C) within the coupling element 6, wherein each of the conductive elements (18A-18C) are connected to a sensor 10A-10C within the second portion.

FIG. 9 illustrates the coupling element 6 where a shield element 32 is twisted around the electrically conductive elements (18A, 18B).

FIGS. 10a-10b illustrates different example of the shield element 32. FIG. 10a shows the shield element 32 being terminated to ground 34 within the first portion 2. FIG. 10b shows the shield element 32 being connected to the wireless interface 16 via a bandpass filter 32.

Figure 11:
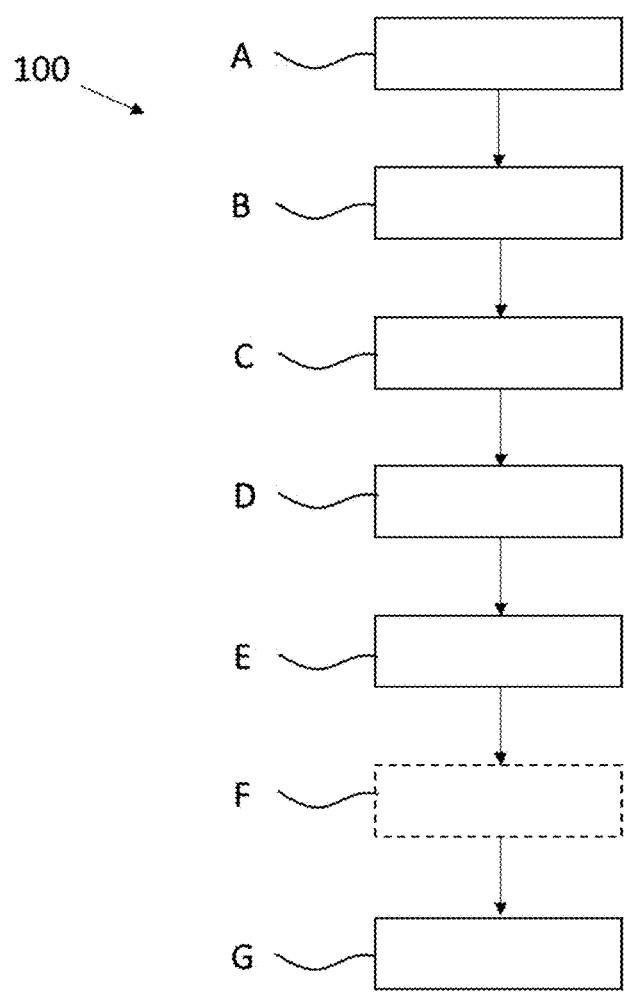
FIG. 11, illustrates a flow diagram of a method.

FIG. 11 illustrates a method 100 for a wireless receiving and/or sending of data in the hearing device 1 comprising the output transducer 10, the coupling element 6 coupling the first portion 2 of the hearing device, the first portion providing a signal and the output transducer is configured to convert the signal to an acoustic output. The method 100 comprising the steps of providing an external antenna part within the coupling element (Step A), providing an internal antenna part, where the internal antenna part includes a first antenna element, a second antenna element where a first end of the second antenna element is arranged at one end of the first antenna element and is connected thereto, and where a second end of the second antenna element is connected to a ground element, and a third antenna element which is spaced at a distance from the second antenna element and connected to the first antenna element (Step B), connecting the internal antenna part to the external antenna part (Step C), supplying a current to the electrically conducting element by a feeding unit and via the internal antenna part (Step D), arranging the first portion behind an ear of a user of the hearing aid (Step E), and receiving and/or sending data by means of the electrically conducting element (Step G). Optionally, the method may further comprise a step of arranging a second portion 4 in an ear canal of the user or on a skin of the user, where the second portion is coupled to the coupling element 6 (Step F).

The invention claimed is:

1. A hearing device comprising;
   a first portion adapted for being arranged behind an ear of a user for providing a signal,
   an output transducer for converting the signal to an acoustic output,
   a coupling element coupled to the first portion, and wherein the coupling element is adapted for transmitting at least the signal or the acoustic output,
   an antenna comprising an external antenna part and an internal antenna part, where the internal antenna part includes a first antenna element, a second antenna element, where a first end of the second antenna element is arranged at one end of the first antenna element and is connected thereto, and where a second end of the second antenna element is connected to a ground plane, and a third antenna element which is spaced at a distance from the second antenna element and connected to the first antenna element,
   a feeding unit configured to supply a current to the antenna via the third antenna element,
   a wireless interface for receiving and/or sending data by means of the antenna, and wherein the coupling element comprises the external antenna part, and where the external antenna part is connected to the internal antenna part, and wherein the coupling element comprises an electrically conducting element coupled to the wireless interface, and wherein the electrically conducting element is at least a part of the external antenna part.

2. A hearing device according to claim 1, comprising a second portion adapted for being arranged distantly from the first portion and for providing the acoustic output to the user, and wherein the coupling element coupling the first portion and the second portion, and wherein the coupling element is adapted for transmitting at least the signal and/or the acoustic output.

3. A hearing device according to claim 1, comprising an external part being arranged distantly to the first portion, and wherein the external part includes an implant stimulator where the coupling element or a second coupling element is coupling the first portion and the external part, and wherein the coupling element or the second coupling element is adapted for transmitting at least the signal, and wherein the second coupling element comprises an electrically conducting element coupled to the wireless interface, and wherein the electrically conducting element is at least a part of the external antenna part.

4. A hearing device according to claim 2, wherein the second portion is arranged in an ear canal of the user, and wherein the second portion includes the output transducer, and/or the external part is arranged on a skin part of the user.

5. A hearing device according to claim 1, wherein the first antenna element, the second antenna element and the third antenna element are formed by an electrically conducting path mounted on a conducting plate, where the electrically conducting path is connected to the electrically conducting element of the external antenna part.

6. A hearing device according to claim 1, wherein the distance between the third antenna element and the second antenna element is determined based on the ratio between the voltage of a voltage distribution and a current of a current distribution along the first antenna element and the second antenna element.

7. A hearing device according to claim 1, wherein an electrical length of the first antenna element, the second antenna element and the external antenna part is in total $\lambda/4$ or $\lambda/4+x*\lambda/2$, where x is a number, such as 0, 1, 2, 3 etc., or the electrical length of the first antenna element, the second antenna element and the electrically conducting element(s) is in total $\lambda/4$ or $x*\lambda/4+/-\lambda/2$, where x is an odd number such as 3, 5, 7etc.

8. A hearing device according claim 1, wherein an electrical length of the ground plane is $\lambda/4$ or $\lambda/4+x*\lambda/2$, where x is a number, such as 0, 1, 2, 3 etc.

9. A hearing device according to claim 1, wherein the internal antenna part comprises a fourth antenna element and a fifth antenna element, where a first end of the fifth antenna element is arranged at one end of the fourth antenna element and is connected thereto, and where a second end of the fifth antenna element is connected to the first antenna element, and where the fourth antenna element is partly parallel with the first antenna element, and where the electrical length of the fourth antenna element is larger than the electrical length of the first antenna element.

10. A hearing device according to claim 1, wherein the antenna comprises an internal parasitic element, and where the feeding unit is further configured to supply the current to the internal parasitic element via a wireless coupling, such as a magnetic coupling or a capacitive coupling.

11. A hearing device according to claim 10, wherein the current within the feeding unit is magnetically coupled to the internal parasitic element.

12. A hearing device according to claim 10, wherein the ground plane is guiding the current from the feeding unit along a length of the ground plane, and wherein the internal parasitic element is positioned within the hearing device such that the current guided by the ground plane is coupled magnetically and/or capacitive to the internal parasitic element.

13. A hearing device according to claim 10, wherein an electrical length of the internal parasitic element is $\lambda/4$ or $\lambda/4+x*\lambda/2$, where x is a number, such as 0, 1, 2, 3 etc.

14. A hearing device according to claim 10, wherein the internal parasitic element is positioned such that a capacitive coupling is provided between the internal parasitic element and the external antenna part, where the capacitive coupling comprises a current being transferred from the external antenna part to the parasitic element.

15. A hearing device according to claim 1, wherein the electrically conducting element is at least adapted for carrying the signal upon transmission to the output transducer.

16. A hearing device according to claim 2, wherein the external antenna part comprises multiple electrically conducting elements, where two or more electrically conducting elements are connected to one or more electronic devices mounted within the second portion or the external part of the hearing device, and where each of the electrically conducting elements are at least adapted for carrying a signal provided by the first portion to the connected electronic device.

17. A hearing device according to claim 16, wherein the two or more electrically conducting elements are terminated within the second portion, external part or within the coupling element (or within the second coupling element).

18. A hearing device according to claim 16, wherein the electronic device(s) within the second portion is a transducer, such as another output transducer or a microphone, and/or a sensor, and/or a light emitting diode and/or an electrode and/or a photodetector.

19. A hearing device according to claim 1, wherein the wireless interface is adapted for receiving and/or sending data by electromagnetic radiation in the frequency range of about 2.45 GHz to about 5.5 GHz, or between 2.44 GHz to 5.5 GHz or about the frequency of 2,45 GHz or about the frequency of 5.5 GHz.

20. A hearing device according to claim 1, wherein the coupling element comprises one or more shield elements for shielding the external antenna part.

21. A hearing device according to claim 20, wherein the shield element is connected to the wireless interface via a bandpass filter, or the shield element is connected to a ground element within the first portion.

22. A hearing device according to claim 1, wherein the feeding unit is configured to supply the current to a second antenna being at least part of the antenna, and wherein the external antenna part and the second antenna are electrically coupled together by a capacitive coupling or a magnetic coupling so that the second antenna is able to extend the operation of the external antenna part.

23. A method for a wireless receiving and/or sending of data in a hearing device comprising an output transducer, a coupling element coupling a first portion of the hearing device, the first portion providing a signal and the output transducer is configured to convert the signal to an acoustic output, the method comprising the steps of:

providing an external antenna part within the coupling element, where the external antenna part is part of an antenna, providing an internal antenna part being part of the antenna, where the internal antenna part includes a first antenna element, a second antenna element where a first end of the second antenna element is arranged at one end of the first antenna element and is connected thereto, and where a second end of the second antenna element is connected to a ground element, and a third antenna element which is spaced at a distance from the second antenna element and connected to the first antenna element, connecting the internal antenna part to the external antenna part, supplying a current to the external antenna part by a feeding unit and via the internal antenna part, arranging the first portion behind an ear of a user of the hearing aid, and receiving and/or sending data by the antenna.

* * * * *